(12) United States Patent
Aoki et al.

(10) Patent No.: US 11,129,539 B2
(45) Date of Patent: Sep. 28, 2021

(54) PULSE MEASURING DEVICE AND CONTROL METHOD THEREOF (71) Applicant: OMRON Corporation, Kyoto (JP)

(72) Inventors: Hiromatsu Aoki, Suita (JP); Masao Hiramoto, Katano (JP); Tomoaki Kimura, Fujisawa (JP)

(73) Assignee: OMRON Corporation, Kyoto (JP)

( * ) Notice: Subject to any disclaimer, the term of this patent is extended or adjusted under 35 U.S.C. 154(b) by 426 days.

(21) Appl. No.: 15/683,852

(22) Filed: Aug. 23, 2017

(65) Prior Publication Data

US 2017/0347898 A1    Dec. 7, 2017

Related U.S. Application Data

(63) Continuation of application No. PCT/JP2015/086390, filed on Dec. 25, 2015.

(30) Foreign Application Priority Data

Mar. 5, 2015 (JP) .............................. JP2015-043897

(51) Int. Cl.
*A61B 5/00* (2006.01)
*A61B 5/024* (2006.01)
*A61B 5/0245* (2006.01)

(52) U.S. Cl.
CPC ............ *A61B 5/0245* (2013.01); *A61B 5/726* (2013.01); *A61B 5/0077* (2013.01);
(Continued)

(58) Field of Classification Search
CPC ..... A61B 5/0245; A61B 5/726; A61B 5/7257; A61B 5/02416; A61B 5/00777; A61B 5/6898
See application file for complete search history.

(56) References Cited

U.S. PATENT DOCUMENTS 9,095,266 B1* 8/2015 Fu ......................... A61B 5/0476
2005/0010139 A1* 1/2005 Aminian .............. A61B 5/1038
600/595

(Continued)

FOREIGN PATENT DOCUMENTS

JP 2010-264095 A 11/2010
JP 2014-198202 A 10/2014

OTHER PUBLICATIONS

Mitchell, H. B. (2010). Image Fusion Theories, Techniques and Applications. Berlin: Springer Berlin (Year: 2010).*

(Continued)

*Primary Examiner* — Serkan Akar
*Assistant Examiner* — Aminah Asghar
(74) *Attorney, Agent, or Firm* — Metrolex IP Law Group, PLLC (57) ABSTRACT

A pulse measuring device includes: an image acquisition unit that acquires plural pieces of time-series photographed image data obtained by photographing a living body; an image processor that generates plural pieces of transformed image data corresponding to the plural pieces of photographed image data by performing a multiple resolution analysis on each of the plural pieces of photographed image data a plurality of times, each of the plural pieces of photographed image data being decomposed into a high-resolution component and a low-resolution component on the multiple resolution analysis; and a pulse measuring unit that calculates a feature quantity indicating luminance of a predetermined area in each of the plural pieces of transformed image data, calculates a variation period of the feature quantity by analyzing time-series data of the feature quantity, and calculates a pulse of the living body based on the variation period of the feature quantity.

5 Claims, 4 Drawing Sheets

(52) U.S. Cl.
CPC ......... *A61B 5/02416* (2013.01); *A61B 5/6898* (2013.01); *A61B 5/7257* (2013.01)

(56) References Cited

U.S. PATENT DOCUMENTS

| | | | |
|---|---|---|---|
| 2006/0149154 A1* | 7/2006 | Stephens | A61B 5/0059 600/504 |
| 2008/0045847 A1 | 2/2008 | Farag et al. | |
| 2013/0096439 A1* | 4/2013 | Lee | A61B 5/024 600/479 |
| 2014/0200460 A1* | 7/2014 | Johnson | A61B 5/0077 600/479 |
| 2014/0303454 A1* | 10/2014 | Clifton | A61B 5/0205 600/301 |
| 2015/0220486 A1* | 8/2015 | Karakonstantis | G06F 17/141 708/205 |

OTHER PUBLICATIONS

Neal Wadhwa et al., "Phase-Based Video Motion Processing", ACM Transactions on Graphics, Jul. 2013, 9 pages, vol. 32, No. 4, Article 80.

Sergey Y. Chekmenev et al., "Multiresolution Approach for Non-Contact Measurements of Arterial Pulse using Thermal Imaging", Proceedings of the 2006 Conference on Computer Vision and Pattern Recognition Workshop (CVPRW'06), Jun. 2006, p. 129-137.

Shoichiro Tomii et al., "Heartbeat Detection by Using Doppler Radar with Wavelet Transform Based on Scale Factor Learning", IEICE Technical Report, Apr. 16, 2014 (received date), 6 pages, vol. 113, No. 456.

International Search Report of PCT/JP2015/086390 dated Mar. 29, 2016.

English translation of Written Opinion of PCT/JP2015/086390 dated Mar. 29, 2016 from the International Searching Authority.

* cited by examiner

Area (X14,Y12)

FIG. 4

PULSE MEASURING DEVICE AND CONTROL METHOD THEREOF

CROSS-REFERENCE TO RELATED APPLICATION

This application is a continuation application of International Application No. PCT/JP2015/086390, filed on Dec. 25, 2015, which claims priority based on the Article 8 of Patent Cooperation Treaty from prior Japanese Patent Application No. 2015-043897, filed on Mar. 5, 2015, the entire contents of which are incorporated herein by reference.

FIELD

The disclosure relates to a pulse measuring device and a control method thereof.

BACKGROUND

Methods for measuring a pulse of a living body include a method for measuring the pulse by bringing a measuring instrument into contact with the living body. Examples of the method include a method for measuring the pulse using an electro cardiogram (electro cardiogram method) and a method for irradiating a peripheral blood vessel of a finger or an earlobe with an infrared ray and measuring the pulse substantially equivalent to a heartbeat from a periodical variation of light reflected from the peripheral blood vessel due to a flood flow and a light absorption characteristic (photoelectric pulse wave method).

Methods for measuring the pulse by not bringing the measuring instrument into contact with the living body include a method for acquiring the pulse through image processing using an image that is obtained by photographing the living body. For example, there is a method for extracting a living body area in the image to detect the pulse from a time-series change of a pixel value in the living body area. JP 2014-198202 A discloses a method for dividing the image in the living body area into plural blocks, calculating a representative value of the pixel values of pixels included in each block, extracting the block in which a difference in representative value of the corresponding block between frames is less than or equal to a threshold, and detecting the pulse of the living body from the pixel value of the pixel included in the extracted block. There is also disclosed a method for performing a wavelet transform on each frame of a video image to acquire a high-frequency image, taking out a spatial phase component by performing a Fourier transform of the high-frequency image in units of pixels, and generating time-series data of a spatial phase to generate the image in which a micromotion amount between the frames is emphasized (see N. Wadhwa, M. Rubinstein, F. Durand, and W. T. Freeman, "Phase-based video motion processing", ACM Trans. Graph., 32(4):80:1-80:10, 2013).

In the technology disclosed in JP 2014-198202 A, for example, the block of a cheek or a forehead having the small spatial change in pixel value is extracted, and a signal of the time-series data of the pixel value is transformed into a frequency component for a constant time interval, such as 30 seconds or 1 minute. For example, the Fourier transform is used in the transform into the frequency component. A peak is detected in a frequency band of the pulse based on a transform result, which allows the detection of the pulse. However, a calculation amount increases in the Fourier transform, particularly there is a problem in that it takes a time to calculate the Fourier transform of the signal of the two-dimensional data in an image analysis. Similarly, in the technology disclosed in N. Wadhwa, M. Rubinstein, F. Durand, and W. T. Freeman, "Phase-based video motion processing", ACM Trans. Graph., 32(4):80:1-80:10, 2013, a two-dimensional Fourier transform is required in each frame, and there is the problem in that the calculation amount increases to take time for processing.

SUMMARY

One or more embodiments may improve a processing speed in the pulse measuring device that measures the pulse based on the image analysis.

According to one or more embodiments, a pulse measuring device includes: an image acquisition unit configured to acquire plural pieces of time-series photographed image data obtained by photographing a living body; an image processor configured to generate plural pieces of transformed image data corresponding to the plural pieces of photographed image data by performing a multiple resolution analysis on each of the plural pieces of photographed image data plural times, each of the plural pieces of photographed image data being decomposed into a high-resolution component and a low-resolution component on the multiple resolution analysis; and a pulse measuring unit configured to calculate a feature quantity indicating luminance of a predetermined area in each of the plural pieces of transformed image data, calculate a variation period of the feature quantity by analyzing time-series data of the feature quantity, and calculate a pulse of the living body based on the variation period of the feature quantity.

According to one or more embodiments, a pulse measuring device control method comprising the steps of: acquiring plural pieces of time-series photographed image data obtained by photographing a living body; generating plural pieces of transformed image data corresponding to the plural pieces of photographed image data by performing a multiple resolution analysis on each of the plural pieces of photographed image data plural times, each of the plural pieces of photographed image data being decomposed into a high-resolution component and a low-resolution component on the multiple resolution analysis; and calculating a feature quantity indicating luminance of a predetermined area in each of the plural pieces of transformed image data, calculating a variation period of the feature quantity by analyzing time-series data of the feature quantity, and calculating a pulse of the living body based on the variation period of the feature quantity.

In one or more embodiments, the processing speed can be improved in the pulse measuring device that measures the pulse based on the image analysis.

DETAILED DESCRIPTION

Hereinafter, a pulse measuring device according to one or more embodiments and a control method thereof will be described in detail with reference to the drawings. The embodiments do not limit the disclosed technology. The embodiments can properly be combined within a consistent range of processing content.

Embodiment

Figure 1:
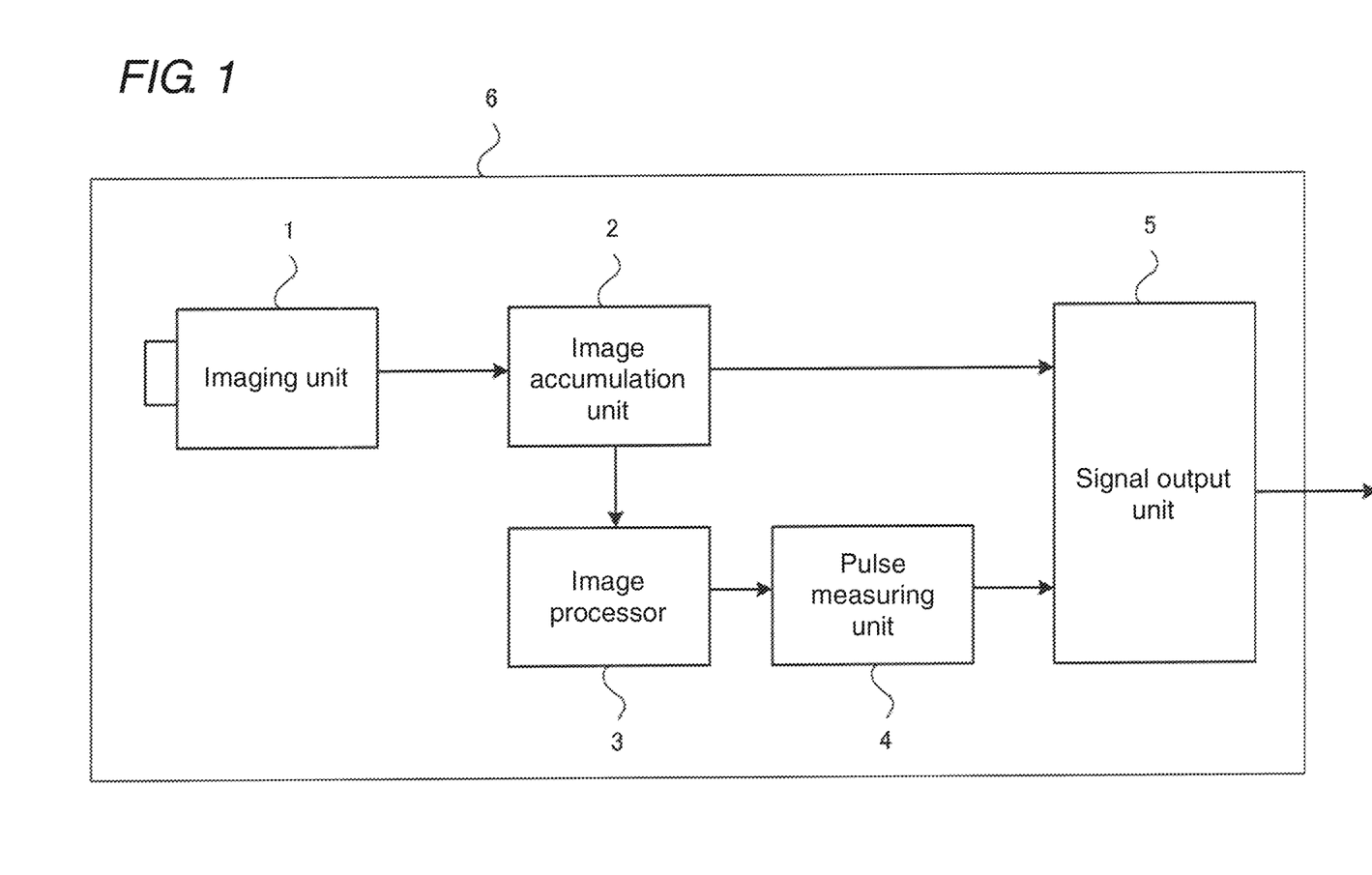
FIG. 1 is a functional block diagram illustrating a schematic configuration of a pulse measuring device according to one or embodiments.

FIG. 1 is a conceptual view illustrating a schematic configuration of a pulse measuring device 6 according to one or more embodiments. The pulse measuring device 6 according to one or more embodiments performs pulse measuring processing of measuring a pulse of a subject, namely, a variation in blood volume associated with pulsation of a heart using an image in which a living body of the subject is photographed without bringing a measuring instrument into contact with the subject under general environmental light such as sunlight and indoor light.

In the embodiment, as illustrated in FIG. 1, the pulse measuring device 6 includes an imaging unit 1, an image accumulation unit 2, an image processor 3, a pulse measuring unit 4, and a signal output unit 5.

The pulse measuring device 6 can be mounted by installing a program or software, which causes a computer to execute a function or processing of each block, on the computer. The program, a recording medium in which the program is recorded, and the computer on which the program is installed are included in one or more embodiments. In the pulse measuring device 6, the function of each block in FIG. 1 may be mounted as dedicated hardware. Alternatively, the pulse measuring device 6 may be mounted as a function extension board that adds the function of each block to the computer. The program can be provided as package software or online software. The program is installed on mobile communication terminals such as a smartphone, a mobile phone, a PHS (Personal Handyphone System), and portable terminal devices including a computer, a digital camera, a tablet terminal, a slate terminal, which have no capability of connection to a mobile communication network, whereby these terminals can act as the pulse measuring device 6. In addition to the functional units in FIG. 1, the pulse measuring device 6 can include various functional units included in a general computer. For example, the pulse measuring device 6 may further include input and output devices such as a keyboard, a mouse, and a display, posture control devices such as an acceleration sensor and an angular velocity sensor, an antenna, a wireless communication unit connected to the mobile communication network, and communication devices such as a GPS (Global Positioning System) receiver.

The imaging unit 1 is a general camera on which an imaging element such as a CCD (Charge Coupled Device) and a CMOS (Complementary Metal Oxide Semiconductor) is mounted. For example, at least three kinds of light receiving elements of R (red), G (green), and B (blue) can be amounted on the imaging unit 1. The imaging unit 1 outputs image data (photographed image data) obtained by the imaging to the image accumulation unit 2. In the embodiment, the imaging unit 1 is included in the pulse measuring device 6 by way of example. Alternatively, an external imaging device may be connected to the pulse measuring device 6 through a wired or wireless communication line. In the case that the photographed image data can be acquired from the storage device included in the pulse measuring device 6, or in the case that the photographed image data can be acquired from a network or a portable recording medium, the pulse measuring device 6 needs not to include the imaging unit 1. The imaging unit 1 may be an infrared camera. In this case, a blood flow in the living body can be photographed, and the photographing can be performed while hardly affected by disturbance of the environmental light.

In the embodiment, it is assumed that the imaging unit 1 is a monochrome CCD camera that photographs a rectangular image of 512 pixels×512 pixels. It is assumed that the imaging unit 1 can output 8-bit (pixel values of 0 to 255) photographed image data at a frame rate of 6 frames/second. It is assumed that 64 frames of the pieces of photographed image data are output in one-time photographing. That is, the imaging unit 1 outputs the pieces of photographed image data obtained by photographing a photographic subject for about 10.7 seconds to the image accumulation unit 2. The specifications such as the image size, the number of bits, and the frame rate are described by way of example. In the embodiment, because the case that the pulse of a human is measured is described by way of example, the frame rate is set to a degree in which the pulse (60 to 80 times/minute) of the human is sufficiently grasped.

The image accumulation unit (image acquisition unit) 2 is a frame memory that acquires the photographed image data from the imaging unit 1 and stores the photographed image data therein. The image accumulation unit 2 is a RAM (Random Access Memory) or an HDD (Hard Disk Drive).

In the embodiment, it is assumed that the image accumulation unit 2 can hold the photographed image data having a frame size of 512 pixels×512 pixels up to 1800 frames.

The image processor 3 acquires the photographed image data from the image accumulation unit 2, performs a multiple resolution analysis of the photographed image data to generate an image having a high-resolution component and an image having a low-resolution component, and outputs the images to the pulse measuring unit 4. The image processor 3 repeatedly performs the multiple resolution analysis plural times.

In the embodiment, it is assumed that the image processor 3 performs the wavelet transform on the photographed image data acquired from the image accumulation unit 2 using a Haar basis twice. The basis selecting method and the number of times of the wavelet transform are described by way of example. The repetitive time of the wavelet transform is not limited to twice as long as the repetitive time is plural times.

The wavelet transform performed on the photographed image data by the image processor 3 will be described with reference to FIG. 3.

Figure 3A:
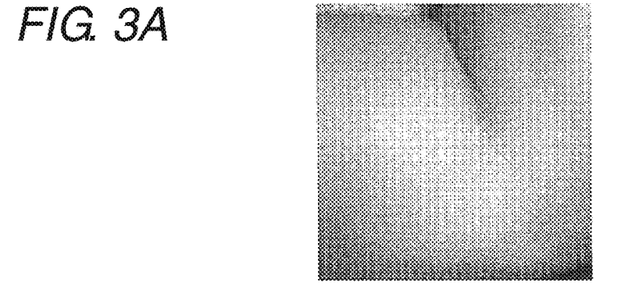
FIGS. 3A to 3D are diagrams illustrating examples of images that are obtained in such a way that a pulse measuring device according to one or more embodiments performs a wavelet transform.

FIG. 3A illustrates an example of the photographed image data input from the image accumulation unit 2. The photographed image data is one of 64 pieces of photographed image data obtained by photographing a skin of the subject with the monochrome CCD camera of the imaging unit 1, and is the image data having the frame size of 512 pixels× 512 pixels as described above.

Figure 3B:
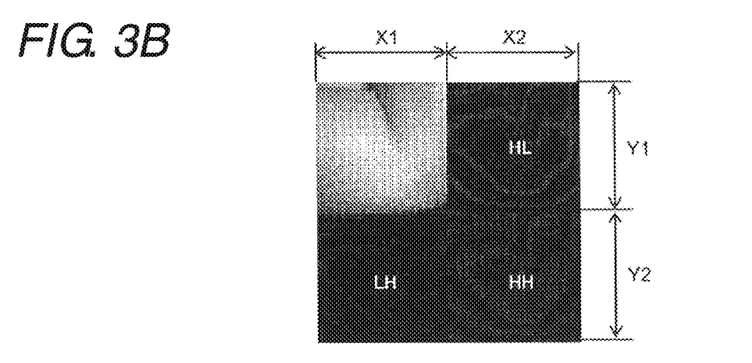

FIG. 3B illustrates the image data (first transformed image data) that is generated in such a way that the image processor 3 performs the first-time wavelet transform on the photographed image data in FIG. 3A. The image processor 3 decomposes the photographed image data into Low-Low (LL), High-Low (HL), Low-High (LH), and High-High (HH) components through the first-time wavelet transform. In FIG. 3B, an area (X1,Y1) expresses the LL component, an area (X2,Y1) expresses the HL component, an area (X1,Y2) expresses the LH component, and an area (X2,Y2) expresses the HH component. The first transformed image data is constructed with 4 areas each of which has a size of 256 pixels×256 pixels.

Figure 3C:
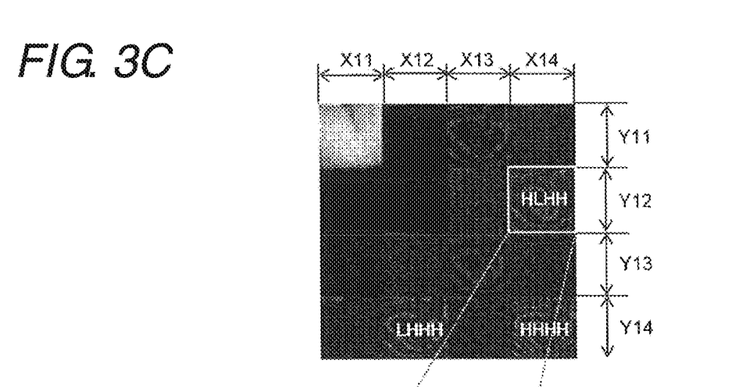

FIG. 3C illustrates the image data (second transformed image data) that is generated in such a way that the image processor 3 performs the second-time wavelet transform on the first transformed image data in FIG. 3B. In the second-time wavelet transform, the image processor 3 further decomposes each component of the first transformed image data in FIG. 3B into LL, HL, LH, and HH components. Resultantly, second transformed image data constructed with a total of 16 areas of area (X11,Y11) to area (X14,Y14) is calculated as illustrated in FIG. 3C. The second transformed image data is constructed with 16 areas each of which has a size of 128 pixels×128 pixels. The image processor 3 generates plural pieces of time-series transformed image data by performing the multiple resolution analysis on each of plural pieces of time-series photographed image data acquired from the image accumulation unit 2, and outputs the plural pieces of time-series transformed image data to the pulse measuring unit 4. At this point, the image processor 3 generates 64 pieces of time-series second transformed image data by performing the wavelet transform on each of 64 pieces of time-series photographed image data twice, and outputs the 64 pieces of time-series second transformed image data to the pulse measuring unit 4.

In the embodiment, by way of example, the wavelet transform is further performed on each of the 4 areas of the first transformed image data to generate the 16 areas of the second transformed image data. As described later, the pulse is calculated using a pixel value of an area (X14,Y12) in the 16 areas of the second transformed image data. Therefore, the second-time wavelet transform may be performed only on the area (X2,Y1) in the 4 areas of the first transformed image data.

The pulse measuring unit 4 acquires plural pieces of time-series transformed image data from the image processor 3, calculates a feature quantity indicating luminance of a specific area in each of the plural pieces of transformed image data, and generates information on the pulse of the subject based on time-series data of the feature quantity. Specifically, the pulse measuring unit 4 analyzes the time-series data of the feature quantity, and generates the information on the pulse of the subject based on periodicity of a luminance change.

Figure 3D:
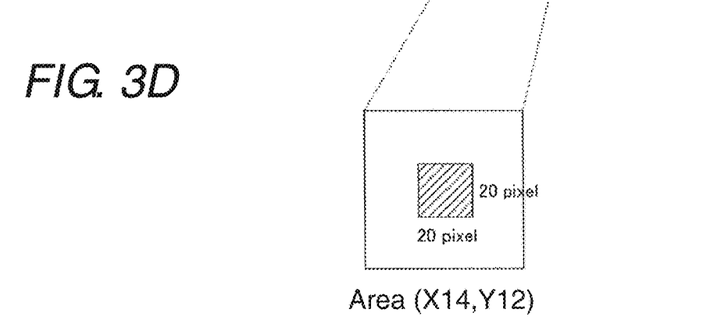

In the embodiment, as illustrated by a hatched portion in FIG. 3D, it is assumed that the specific area is a 20-pixel-by-20-pixel specific area (luminance detection area) located in a central portion of the area (X14,Y12) in the 16 areas of the second transformed image data. The pulse measuring unit 4 calculates an average luminance value of pixels in a luminance detection area with respect to each of the 64 pieces of time-series second transformed image data, and analyzes a time change of the average luminance value.

Figure 4:
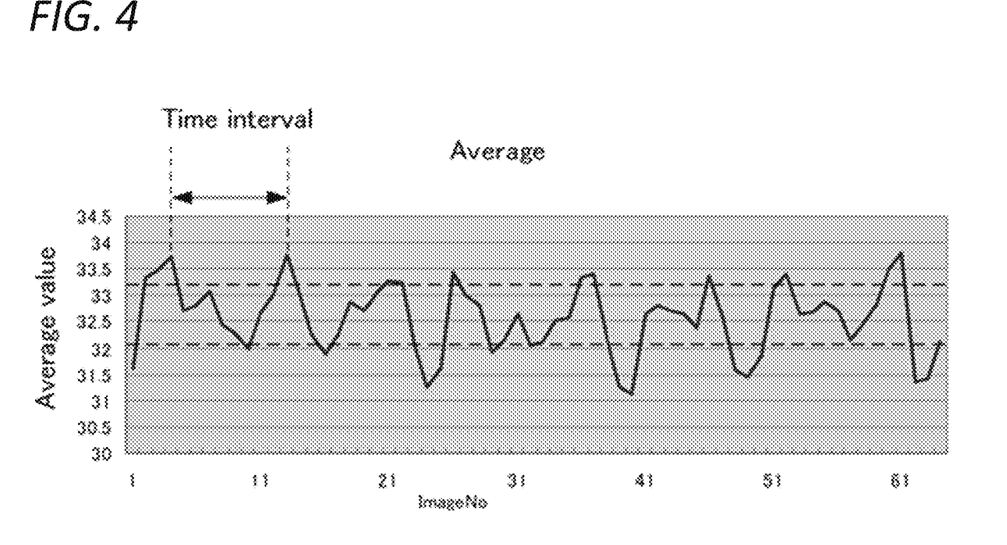
FIG. 4 is a diagram illustrating an example of a time variation of luminance in photographed image data detected by a pulse measuring device according to one or more embodiments.

FIG. 4 is a graph in which the average luminance value of the pixels in the luminance detection area is plotted in time series with respect to each of the 64 pieces of second transformed image data. As illustrated in FIG. 4, the average luminance value changes periodically, and the change of the average luminance value expresses the period of the pulse.

The pulse measuring unit 4 obtains a variation period of the average luminance value. In the example of FIG. 4, the pulse measuring unit 4 detects a peak in the average luminance value of 33.2 or more and an underpeak in the average luminance value or 32.1 or less, and calculates the variation period based on a combination of the peak and the underpeak. The pulse measuring unit 4 calculates the number of pulses from the variation period of the average luminance value. The number of pulses means the number of pulsation times per unit time. In the example of FIG. 4, because of 8 peaks and 8 underpeaks, the pulse is generated 8 times for an image acquisition time interval of 10.7 seconds. Accordingly, the pulse measuring unit 4 calculates the number of pulses of the subject as 45 times/minute. In addition to the number of pulses, the pulse measuring unit 4 may generate an amplitude (pulsation strength), a pulse graph (the graph in FIG. 4), and existence or non-existence of an irregular pulse as pulse information.

For the average luminance value, a threshold used to obtain the peak and the underpeak may be a predetermined fixed value, or adaptively set with respect to the time-series luminance data. For example, a median ±Δv of the time-series luminance data may be used as the threshold. Alternatively, for example, the variation period may be obtained using the Fourier analysis. In this case, because the Fourier analysis is performed on one-dimensional data, there is little influence of an increase in calculation amount, and the variation period can be obtained with higher accuracy.

In the embodiment, the luminance detection area is set to the area (X14,Y12) in the 16 areas of the second transformed image data. Alternatively, the luminance detection area may be set to the area (X14,Y14) or area (X12,Y14) in the 16 areas of the second transformed image data. The luminance detection area may be set to one of the area (X14,Y14) and area (X12,Y14) where the luminance change emerges more clearly. In the pieces of data in the areas, the luminance change of the original photographed image data is emphasized, and a change in light reflected from a body surface of the subject associated with the pulsation, namely, a change in spatial distribution of a luminance gradient is emphasized. The image in each area obtained through the wavelet transforms of the two times indicates a feature corresponding to a rate of change (second order differential) in spatial distribution of the luminance. Therefore, the feature corresponding to the pulsation of the subject emerges on the time-series variation of the average luminance value of the luminance detection area in the second transformed image data. The pulse of the subject can be calculated by analyzing the time variation.

In the pulse measuring method in which the image data is used, the image processing is performed using the wavelet transform having the calculation amount smaller than that of the Fourier transform, so that the processing speed can largely be improved compared with the pulse measuring method in which the Fourier transform is used. As described above, the pulse is calculated based on the luminance in the area (X14,Y12) that is of the partial area of the second transformed image data. In the embodiment, the pulse is further calculated based on the luminance of the pixel in the luminance detection area that is of the partial area in the partial area. Accordingly, the pulse measurement can be performed based on the image with a light processing load at low calculation cost. In the pulse measuring device 6 of the embodiment, the special camera is not required because the pulse can be measured using the general image data obtained by the photographing with a general camera. Accordingly, the pulse can be measured based on the image with no use of a device dedicated to the pulse measurement by installing the program performing the processing of one or more embodiments on a device, such as a smartphone and a digital camera, which includes the general imaging element. Additionally, because of the low calculation cost and high processing speed, even the device having a poor calculation resource can practically be operated. Additionally, the compact device can be mounted at low cost.

In the embodiment, the luminance average value in the luminance detection area is plotted in time series. The luminance detection area is binarized into a black pixel and a white pixel using a threshold, and the number of white pixels may be counted and plotted in time series.

The number of times of the wavelet transform may be at least three times as described above. It is considered that the number of times of the wavelet transform, by which the luminance change emerges most easily in the transformed image data, changes according to the number of pixels of the photographed image data and a spatial scale of the photographed image data. The optimum number of times may be obtained by an experiment and stored in the pulse measuring device, or the user can arbitrary set the optimum number of times. Which component of the image data is used in latter wavelet transform may be changed according to the number of times of the wavelet transform. For example, in the case that the wavelet transform is performed twice, the second-time wavelet transform is performed on the HL, LH, and HH components of the first transformed image data, and the HL, LH, and HH components of the obtained second transformed image data are used in the pulse calculation. For example, in the case that the wavelet transform is performed three times, the second-time wavelet transform is performed on the LL component of the first transformed image data, the third-time wavelet transform is performed on the HL, LH, and HH components of the obtained second transformed image data, and the HL, LH, and HH components of the obtained third transformed image data are used in the pulse calculation. For example, in the case that the wavelet transform is performed four times, the second-time wavelet transform is performed on the LL component of the first transformed image data, the third-time wavelet transform is performed on the LL component of the obtained second transformed image data, the fourth-time wavelet transform is performed on the HL, LH, and HH components of the obtained third transformed image data, and the HL, LH, and HH components of the obtained fourth transformed image data are used in the pulse calculation.

The signal output unit 5 externally outputs the information on the pulse calculated by the pulse measuring unit 4. For example, the information on the pulse may be output as text data, or output as image data displaying numerical data or a numerical value on display devices (not illustrated) such as an LCD (Liquid Crystal Display). The signal output unit 5 may acquire the time-series image data from the image accumulation unit 2, reconfigure the time-series image data into the video image data, and output the video image data.

Figure 2:
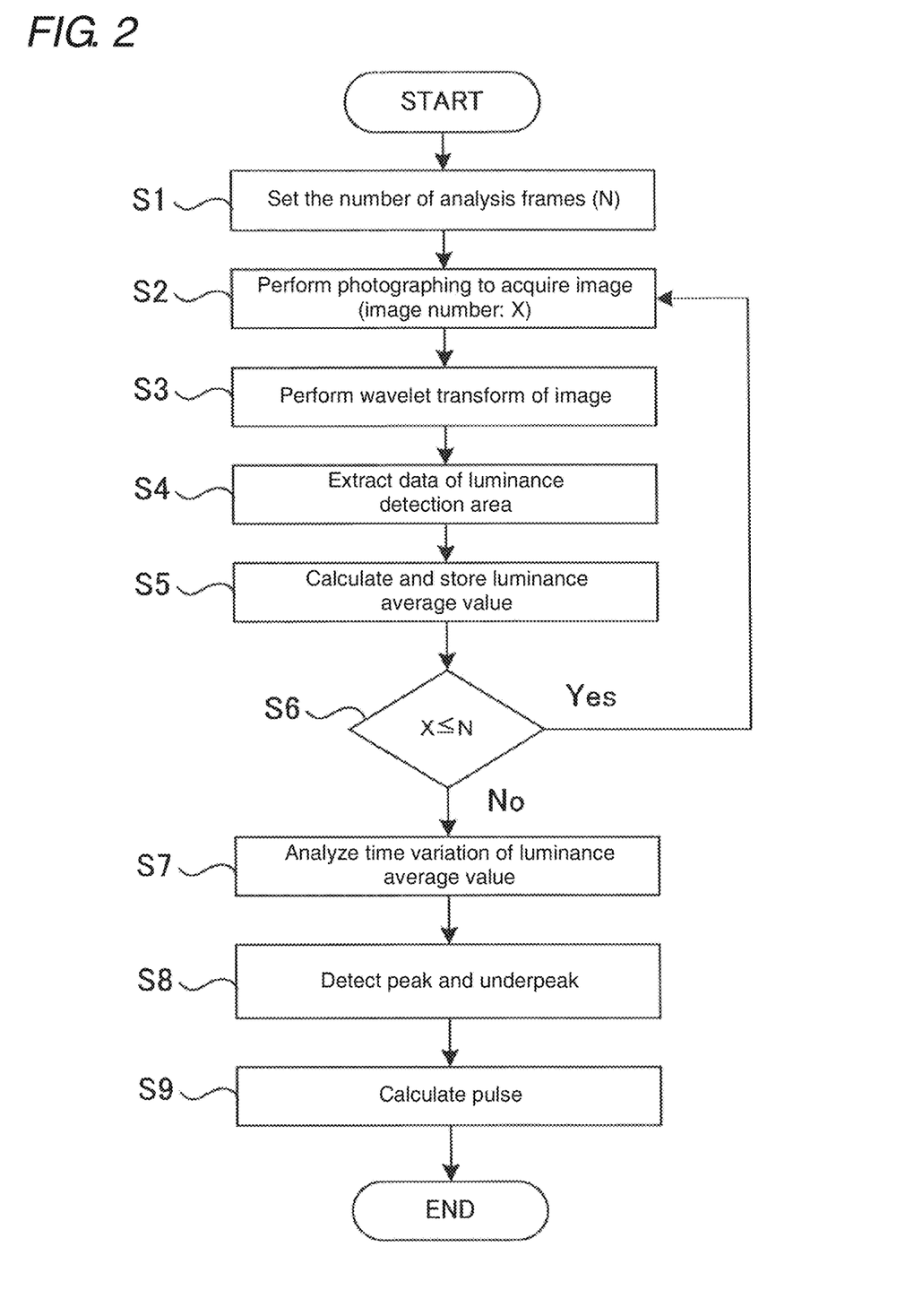
FIG. 2 is a flowchart illustrating a flow of processing performed by a pulse measuring device according to one or more embodiments.

FIG. 2 is a flowchart illustrating a flow of processing performed by the pulse measuring device of the embodiment.

When the processing is started, the number of analysis frames (N) is set in Step S1. The number of analysis frames is one that is acquired as the time-series image data from the imaging unit 1, and the number of analysis frames is 64 in the above example. The number of analysis frames may be a predetermined fixed value, or a setting value input by a user using an input device (not illustrated, such as a keyboard and a touch panel).

In Step S2, the imaging unit 1 performs the imaging, and the image accumulation unit 2 acquires the photographed image data. A photographed image number X is provided to the photographed image data for the purpose of management. The photographed image number X is incremented by one every time the imaging is performed. The image accumulation unit 2 outputs the photographed image data to the image processor 3.

In Step S3, the image processor 3 performs the wavelet transform on the photographed image data twice, and outputs the second transformed image data to the pulse measuring unit 4.

In Step S4, the pulse measuring unit 4 extracts the data of the luminance detection area in the specific area (X14,Y12) of the second transformed image data. In Step S5, the pulse measuring unit 4 calculates the luminance average value of the luminance detection area, and stores a calculation result.

In Step S6, whether the photographed image number X is less than or equal to the number of analysis frames N is determined. The pieces of processing in Steps S2 to S5 are repeatedly performed until X>N. For X>N, the processing goes to Step S7.

In Step S7, the pulse measuring unit 4 analyzes the time variation of the luminance average value based on the plural time-series luminance average values of the number of analysis frames N. Specifically, the pulse measuring unit 4 calculates the variation period by detecting the peak and the underpeak of the luminance average value in Step S8, and calculates the number of pulses based on the variation period in Step S9.

In the flowchart of FIG. 2, the pieces of processing to the calculation of the luminance average value are performed every time the photographing of one frame is performed. Alternatively, after the photographing is performed for the number of analysis frames, the pieces of image data of all the frames may be accumulated in the image accumulation unit 2. In such cases, while the photographing is completed, the image processor 3 and the pulse measuring unit 4 acquire the photographed image data of the processing target from the image accumulation unit 2 one by one, and perform the wavelet transform and the calculation of the luminance average value. For example, the pulse measuring device 6 does not include the imaging unit 1, the photographed image data previously obtained by photographing on the outside is acquired from the network or the portable recording medium, and pulse is measured based on the photographed image data. In such cases, similarly the wavelet transform and the calculation of the luminance average value are performed after the photographing processing in Step S2 is completed. In the embodiment, the photographed image data output from the imaging unit 1 is directly used in the pulse measurement. Alternatively, for example, in the case that the photographic subject such as a skin is photographed only in a part of the image, the pieces of processing from Step S3 may be performed while a part (portion in which the photographic subject is photographed) of the photographed image data is cut out. Preprocessing such as a resolution transform, a luminance adjustment, and a noise removal may be performed on the photographed image data.

The method for measuring the pulse through the image processing having the light processing load using the photographed image data obtained by photographing the skin of the subject is described in the embodiment. In the method of the embodiment, the time variation of the mode of the skin light reflection associated with the change of the blood flow is detected while emphasized through the wavelet transform. One or more embodiments provide the technology of detecting the time variation through the image processing by emphasizing the minute time variation through the wavelet transform, so that a body oscillation associated with the pulsation can be detected from the image. For example, a head of the subject is minutely oscillated by force of a heart sending the blood to an artery. Therefore, the minute oscillation of the head is emphasized by performing the wavelet transform plural times on the photographed image data obtained by photographing a part or whole of the head of the subject, and the pulse can be calculated by detecting the time variation of the minute oscillation. In a region except for the skin of the body, such as hair of the head and an arm, which is minutely oscillated by the blood flow of the artery, the minute time variation of the region is detected by performing the wavelet transform plural times on the photographed image data obtained by photographing the region, and the pulse can be calculated. It is considered that the optimum number of times of the wavelet transform changes according to the photographed image data of the region of the body.

The invention claimed is:

1. A pulse measuring device comprising a processor configured to perform operations comprising:
    acquiring a plurality of pieces of time-series photographed image data obtained by photographing a living body;
    generating a plurality of pieces of transformed image data, in which a luminance change of the plurality of pieces of time-series photographed image data is emphasized for a luminance detection area, corresponding to the plurality of pieces of time-series photographed image data by performing a multiple resolution analysis on each of the plurality of pieces of time-series photographed image data a plurality of times, each of the plurality of pieces of time-series photographed image data being decomposed into a high-resolution component and a low-resolution component in the multiple resolution analysis;
    for each of the plurality of pieces of the time-series photographed image data, setting, as the luminance detection area, a predetermined area in a first partial area of a first image comprising a first high-resolution component, the first image comprising transformed image data generated through a current multiple resolution analysis on a second partial area of a second image comprising a second high-resolution component, the second image comprising transformed image data generated through a previous multiple resolution analysis on the plurality of pieces of time-series photographed image data;
    calculating a feature quantity indicating luminance of the predetermined area in each of the plurality of pieces of transformed image data, calculating a time interval of the feature quantity by analyzing time-series data of the feature quantity, and calculating a pulse of the living body based on the time interval of the feature quantity; and
    calculating an average value of luminance values of pixels included in the predetermined area as the feature quantity.

2. The pulse measuring device according to claim 1, wherein the processor is configured to perform operations further comprising detecting a peak in the feature quantity of a first threshold or more, detecting an underpeak in the feature quantity of a second threshold or less, and calculating the time interval of the feature quantity based on the detected peak and underpeak.

3. The pulse measuring device according to claim 1, wherein the processor is configured to perform operations further comprising calculating the time interval of the feature quantity by performing a Fourier analysis on the time-series data of the feature quantity.

4. A pulse measuring device control method comprising:
    acquiring a plurality of pieces of time-series photographed image data obtained by photographing a living body;
    generating a plurality of pieces of transformed image data, in which luminance change of the plurality of pieces of time-series photographed image data is emphasized for a luminance detection area, corresponding to the plurality of pieces of time-series photographed image data by performing a multiple resolution analysis on each of the plurality of pieces of time-series photographed image data a plurality of times, each of the plurality of pieces of time-series photographed image data being decomposed into a high-resolution component and a low-resolution component in the multiple resolution analysis;
    for each of the plurality of pieces of the time-series photographed image data, setting, as the luminance detection area, a predetermined area in a first partial area of a first image comprising a first high-resolution component, the first image comprising transformed image data generated through a current multiple resolution analysis on a second partial area of a second image comprising a second high-resolution component, the second image comprising transformed image data generated through a previous multiple resolution analysis on the plurality of pieces of time-series photographed image data;
    calculating a feature quantity indicating luminance of the predetermined area in each of the plurality of pieces of transformed image data, calculating a time interval of the feature quantity by analyzing time-series data of the feature quantity, and calculating a pulse of the living body based on the time interval of the feature quantity; and calculating an average value of luminance values of pixels included in the predetermined area as the feature quantity.

5. A non-transitory computer-readable storage medium storing a program configured to cause a computer to perform a pulse measuring device control method comprising:
    acquiring a plurality of pieces of time-series photographed image data obtained by photographing a living body;
    generating a plurality of pieces of transformed image data, in which luminance change of the plurality of pieces of time-series photographed image data is emphasized for a luminance detection area, corresponding to the plurality of pieces of time-series photographed image data by performing a multiple resolution analysis on each of the plurality of pieces of time-series photographed image data a plurality of times, each of the plurality of pieces of time-series photographed image data being decomposed into a high-resolution component and a low-resolution component in the multiple resolution analysis;
    for each of the plurality of pieces of the time-series photographed image data, setting, as the luminance detection area, a predetermined area in a first partial area of a first image comprising a first high-resolution component, the first image comprising transformed image data generated through a current multiple resolution analysis on a second partial area of a second image comprising a second high-resolution component, the second image comprising transformed image data generated through a previous multiple resolution analysis on the plurality of pieces of time-series photographed image data;

calculating a feature quantity indicating luminance of the predetermined area in each of the plurality of pieces of transformed image data, calculating a time interval of the feature quantity by analyzing time-series data of the feature quantity, and calculating a pulse of the living body based on the time interval of the feature quantity; and calculating an average value of luminance values of pixels included in the predetermined area as the feature quantity.

* * * * *